(12) United States Patent
Amling et al.

(10) Patent No.: US 8,194,122 B2
(45) Date of Patent: *Jun. 5, 2012

(54) UNIVERSAL SCOPE READER

(75) Inventors: Marc R. Amling, Santa Barbara, CA (US); David Chatenever, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1646 days.

This patent is subject to a terminal disclaimer.

(21) Appl. No.: 11/542,461

(22) Filed: Oct. 3, 2006

(65) Prior Publication Data

US 2007/0030345 A1 Feb. 8, 2007

Related U.S. Application Data

(63) Continuation-in-part of application No. 10/095,616, filed on Mar. 12, 2002, now Pat. No. 7,289,139.

(51) Int. Cl.
 *H04N 7/18* (2006.01)
(52) U.S. Cl. ............................................ 348/65; 348/61
(58) Field of Classification Search .................... 348/61, 348/65
See application file for complete search history.

(56) References Cited

U.S. PATENT DOCUMENTS

| | | | |
|---|---|---|---|
| 4,777,947 A | 10/1988 | Zwick | |
| 5,492,527 A | 2/1996 | Glowa et al. | |
| 5,592,727 A | 1/1997 | Glowa | |
| 5,630,180 A | 5/1997 | Kusaka | |
| 5,669,921 A | 9/1997 | Berman et al. | |
| 5,810,858 A | 9/1998 | Berman et al. | |
| 5,896,166 A | 4/1999 | D'Alfonso et al. | |
| 5,910,776 A | 6/1999 | Black | |
| 6,053,928 A | 4/2000 | Van Wyk et al. | |
| 6,092,722 A | 7/2000 | Heinrichs et al. | |
| 6,141,037 A | 10/2000 | Upton et al. | |
| 6,217,598 B1 | 4/2001 | Berman et al. | |
| 6,295,082 B1 | 9/2001 | Dowdy et al. | |
| 6,313,868 B1 | 11/2001 | D'Alfonso et al. | |
| 6,328,752 B1 | 12/2001 | Sjostrom et al. | |
| 6,364,827 B1 | 4/2002 | Irion et al. | |
| 6,419,684 B1 | 7/2002 | Heisler et al. | |
| 6,436,032 B1 | 8/2002 | Eto et al. | |
| 6,638,212 B1 | 10/2003 | Oshima | |
| 7,237,990 B2 | 7/2007 | Deng | |
| 7,247,161 B2 | 7/2007 | Johnston et al. | |
| 7,289,139 B2 | 10/2007 | Amling et al. | |
| 7,887,559 B2 | 2/2011 | Deng et al. | |

(Continued)

FOREIGN PATENT DOCUMENTS

DE 197 23 442 2/1998

(Continued)

OTHER PUBLICATIONS

International Search Report and Written Opinion of the International Searching Authority; PCT/US09/43733; Jun. 18, 2009; 8 pages.

(Continued)

*Primary Examiner* — Allen Wong
(74) *Attorney, Agent, or Firm* — St. Onge Steward Johnston & Reens LLC

(57) ABSTRACT

A system for automatically setting video signal processing parameters for an endoscopic video camera system based upon characteristics of an attached endoscope, with reduced EMI and improved inventory tracking, maintenance and quality assurance, and reducing the necessity for adjustment and alignment of the endoscope and camera to achieve the data transfer.

27 Claims, 3 Drawing Sheets

U.S. PATENT DOCUMENTS

| | | |
|---|---|---|
| 2003/0174205 A1 | 9/2003 | Amling et al. |
| 2004/0064019 A1 | 4/2004 | Chang et al. |
| 2004/0252188 A1 | 12/2004 | Stantchev et al. |
| 2004/0267297 A1 | 12/2004 | Malackowski |
| 2006/0149126 A1 | 7/2006 | Ertas et al. |
| 2007/0030345 A1 | 2/2007 | Amling et al. |
| 2009/0030278 A1 | 1/2009 | Minakuchi |

FOREIGN PATENT DOCUMENTS

| | | |
|---|---|---|
| EP | 59069720 | 4/1984 |
| EP | 0 534 198 | 3/1993 |
| EP | 1 155 654 | 11/2001 |
| EP | 1347638 A1 | 9/2003 |
| EP | 1424036 A1 | 6/2004 |
| EP | 1759629 A1 | 3/2007 |
| EP | 1767140 A1 | 3/2007 |
| JP | 2001046326 A | 2/2001 |
| JP | 2001327459 A | 11/2001 |
| JP | 2003325432 A | 11/2003 |
| JP | 2004174008 A | 6/2004 |
| JP | 2006254974 A | 9/2006 |
| WO | WO 97/29678 | 8/1997 |
| WO | 2005115106 A2 | 12/2005 |
| WO | 2009027672 A1 | 3/2009 |
| WO | 2009060460 A2 | 5/2009 |

OTHER PUBLICATIONS

Japanese Office Action; Application No. 2003-066189; Aug. 22, 2006; 2 pages.

Microchip, 1K/2K/4K 1.8V Microwire Serial EEPROM, Microchip Technology Inc., 1996, 12 pages.

European Search Report; Application No. EP 10 17 0427; Sep. 30, 2010; 8 pages.

Medical Connectivity Consulting, "New RFID standard Rubee has health care applications", http://medicalconnectivity.com/2006/09/27/new-rfid-standard-rubee-has-health-care-application, Sep. 27, 2006, 5 pages.

Extended European Search Report, Feb. 8, 2008, 4 Pages.

UNIVERSAL SCOPE READER

CROSS-REFERENCE TO RELATED APPLICATIONS

This application is a continuation-in-part application of U.S. patent application Ser. No. 10/095,616 filed Mar. 12, 2002, now patented as U.S. Pat. No. 7,289,139 issued on Oct. 30, 2007.

FIELD OF THE INVENTION

The invention relates to endoscope video camera systems, where the video camera electronically identifies an attached endoscope and automatically sets system parameters in accordance with certain endoscope parameters. Additionally, the endoscope is electronically identified for manipulating, (i.e., reading information from, updating and then writing information to the endoscope) for the purposes of endoscope use and maintenance, inventory tracking and control, and monitoring of various other endoscope parameters.

BACKGROUND OF THE INVENTION

An endoscope is an elongated, tubular structured medical device that is inserted into body cavities to facilitate examination by medical professionals. The endoscope includes a telescope with an objective lens at its distal end. The telescope includes an image-forwarding system, which in rigid endoscopes is typically a series of spaced-apart lenses. In flexible endoscopes, typically, the image-forwarding system is a bundle of tiny optical fibers assembled coherently Typically, at the proximal end of the image-forwarding system is an ocular lens that creates a virtual image for direct human visualization. Often a camera means, such as a charge coupled device (CCD) chip, is mounted to the endoscope. It receives the image and produces a signal for a video display. While surgeons can, and often do, look directly into the endoscope through an ocular lens, it is more common for them to use an attached camera and observe an image on a video screen. In conventional and video camera arrangements, the camera (hereinafter referred to as a "camera head") is usually detachably connected to the endoscope. A camera control unit (CCU) is employed to provide, among other controls, a link between the camera head and the video display.

Endoscopes come in a variety of sizes for particular applications and surgical procedures. Further, the telescope lens system may have a variety of optical properties. For example, the objective lens may include a prism whereby the image viewed is at some angle with respect to that of the axis of the telescope. Also, different endoscopes may have different fields of view (FOV). These and other variations affect the optical properties of particular endoscopes.

As above noted, the camera head is usually detachable from the endoscope, and is often conveniently constructed so as to be attachable to a variety of endoscopes having differing optical properties. For this reason, a CCU receiving a video signal from an attached camera head will need to know the endoscope optical properties in order to present an optimized image on the video monitor. Currently, the settings of the camera head and CCU are manually adjusted to the endoscope's optical properties.

It would be advantageous to simplify the task of using the endoscope and video camera system by eliminating the need to make manual adjustments to the camera head and/or CCU in order to optimize the video camera system settings for an attached endoscope.

To ensure optimal video system operation utilizing a particular endoscope, it is also necessary that the endoscope undergo periodic scheduled and unscheduled maintenance. Further, most endoscope manufacturers require their products to be maintained properly to assure reliable, accurate and precise functionality. This enhances the manufacturer's reputation and the reliance of health care professionals on the manufacturer's products. From a manufacturer's perspective, it is important that only factory authorized personnel service their products; however, it is a reality in the marketplace that some medical facilities may use unauthorized repair services. It is to a manufacturer's advantage to discourage such suboptimal maintenance because if maintenance is performed incorrectly, medical personnel may attribute problems caused by the incorrectly performed maintenance to the product and/or manufacturing design.

Related to the maintenance of the endoscope are the usage characteristics of the endoscopes. For a manufacturer, how its products are used is valuable information. A manufacturer may want to know, for example, how often each product is used, the elapsed time of each use, the maintenance history of the product, and so on. These factors can impact future endoscope design related to durability, reliability, components and materials used in the manufacturing process.

It is known in the art to utilize electronic sensors to record operating conditions beyond the endoscope's recognized safe operating range to which it has been subjected. Peak values for conditions such as, pressure, humidity, irradiation, and/or shock or impact loads to which the endoscope has been exposed may be recorded. Upon failure of the endoscope, this information may then be utilized to determine the probable cause of the failure.

U.S. Pat. Nos. 5,896,166 to D'Alfonso et al. ("the '166 patent") and 6,313,868 to D'Alfonso et al. ("the '868 patent"), both disclose storing camera parameters and camera use characteristics in a non-volatile memory located in the camera head and transmitting the camera parameters and camera use characteristics to a camera control unit through a data coupling upon connection of the camera unit to a camera control unit. However, neither reference discloses a system where the endoscope has a memory device located in it, so that a single camera unit may be interchanged with a plurality of endoscopes and whereupon connection of the camera unit will automatically read the endoscope parameters and use characteristics. Further, neither the '166 nor the '868 patent discloses a system where the endoscope use characteristics can be updated to log a history of the particular endoscope use. Rather, both the '166 and the '868 patents are limited to updating only the camera unit. Still further, neither the '166 nor the '868 patent discloses a system wherein the endoscope parameters and use characteristics can be read automatically through non-contact transmission.

Another problem in the field of endoscope management is that of keeping track of the many different endoscopes used throughout the facility. There have been various approaches to keeping track of the locations and inventory of endoscopes. Simple inventory control and sign-out sheets are labor intensive and inaccurate, and, as a result, are ineffective for assuring the level of scrutiny that is required for medical equipment. Further, sign-out sheets do not allow for monitoring equipment, for example, determining whether the endoscope is functioning properly or needs maintenance.

Bar codes have been used for tracking purposes. Bar coding of equipment allows identification and locating of the equipment by reading the bar code with a portable bar code scanner. However, bar coding is ineffective when the equipment has been moved since the last time that it was scanned. Moreover, the use of bar codes can require the labor-intensive step of touring the facility with one or more portable scanners in search of endoscopes. Further, bar codes, like sign-out sheets, do not allow for the monitoring of equipment, for example, determining whether the endoscope is functioning properly or needs maintenance.

It is known in the art that energy and data transmission can take place through an inductive coupling in which high frequency coils act like a loosely coupled transformer as disclosed in U.S. Pat. No. 6,092,722 to Heinrichs et al. ("the '722 patent"). The high frequency coil, when power is applied to it, produces a high frequency field, which will be imposed upon the high frequency coil of another device when brought into close proximity.

One major problem with the use of inductive coupling as disclosed in the '722 patent is that it can create unacceptable levels of electro-magnetic interference ("EMI") in the operating room environment. Electronic equipment, such as the video signals transmitted from the camera head to the camera control unit, can be particularly sensitive to EMI. Therefore, to reduce the negative effects of EMI, adequate shielding should be provided. This, however, significantly adds to the cost and manufacturing time of the device. Therefore, a system that does not produce EMI is greatly desired.

Another disadvantage with the use of inductive coupling as disclosed in the '722 patent is that it necessitates the use of inductive coils both in the endoscope and the camera head adding greatly to the size and the weight of the devices. In addition to the added size and weight of the inductive coils, the necessary shielding for the EMI produced by the inductive coils will further increase the device size and weight. Endoscopes and camera heads that are lighter, smaller and easier to handle are desired.

Another disadvantage to the inductive coupling technique as disclosed in the '722 patent is because high frequency coils act like a loosely coupled transformer, both high frequency coils should be aligned one directly on top of the other in order to achieve an effective data transfer. The inductive field created by the high frequency coils is unidirectional and therefore accurate alignment of the component is important. This situation could be very frustrating for medical professionals, having to spend time trying to accurately align the camera head and endoscope to have the video system function properly. Therefore, a system that does not require precise alignment of the components is desired.

Radio frequency identification ("RFID") has been used to locate various devices and/or equipment. However, RFID used in the operating room environment has been limited due to the large power ranges required for locating the device. RFID utilized for locating purposes necessitates using a transceiver with as large a power range as is reasonable. A large power range, unfortunately, may cause receipt of the signal by unintended RFID receivers. That is, if an endoscope is in use in room A, it is undesirable to have unrelated endoscope equipment in room B "respond" to the transceiver. RFID has been limited to tracking the location of devices and/or equipment, facilitating only one-way communication from the device and/or equipment to the recording or tracking system.

While RFID has the advantage of having a relatively rapid read rate, one particular limitation RFID has encountered is accuracy of scans in relatively harsh environments. For example, RFID has been known to struggle with getting an accurate read through or near liquids and metals.

Therefore, a system is needed that simplifies and optimizes endoscope and video camera usage and does not interfere with sensitive electronic equipment, encourages customers to maintain the endoscope to manufacturer's parameters and provides the endoscope manufacturer with information regarding product usage and maintenance.

SUMMARY OF THE INVENTION

The present invention is an endoscope read/write apparatus that stores and provides endoscope parameters and endoscope use history data, utilizing a detachable camera capable of accessing the endoscope parameter data and endoscope use history data, and if required, updating and rewriting endoscope use history data to the endoscope for storage. A transponder/transceiver is affixed to the endoscope, and the endoscope transponder/transceiver is capable of transmitting and receiving wireless signals. The endoscope transponder/transceiver is coupled to a memory device that stores electronic representations of the endoscope parameters and endoscope use history data, and when queried, supplies the electronic representations to the endoscope transponder/transceiver. To transmit wireless signals for communication with the endoscope transponder/transceiver, a camera transponder/transceiver is affixed to the camera and set to receive the endoscope transponder/transceiver transmitted wireless signals.

In one advantageous embodiment, the present invention utilizes wireless transponder/transceivers using either an RFID format or a standard called IEEE 1902.1, which is also known as the "RuBee" format. As such, the problems associated with inductive coupling such as radiated EMI, alignment requirements, and inability to locate the device are absent.

In one advantageous embodiment of the present invention, an endoscope video system is provided for communicating between an endoscope and a detachable camera comprising: a first transponder/transceiver is affixed to the endoscope set to transmit wireless signals containing endoscope parameters and endoscope use history data and set to receive wireless signals containing modified endoscope use history data; a second transponder/transceiver affixed to the detachable camera set to transmit wireless signals containing modified endoscope use history data, and set to receive wireless signals containing the endoscope parameters and endoscope use history data; a memory device coupled to the first transponder/transceiver having memory locations for storing the data contained in the wireless signals; and a camera control unit, coupled to the camera, for receiving and processing the endoscope parameters and endoscope use history data.

In another advantageous embodiment of the present invention, an endoscope video system is provided for the transfer of data from an endoscope comprising: a transponder/transceiver affixed to the endoscope, set to transmit wireless signals containing endoscope parameters and endoscope use history data, and set to receive wireless signals containing modified endoscope use history data; and a memory device coupled to the transponder/transceiver having memory locations for storing the data contained in the wireless signals.

In yet another advantageous embodiment of the present invention, an endoscope video system is provided for automatically adjusting to the parameters of a plurality of endoscopes, and to provide for the transfer of modified endoscope use history data comprising: a transponder/transceiver positioned on a camera head, set to transmit wireless signals containing modified endoscope use history data, and set to receive wireless signals containing endoscope parameters and endoscope use history data; and a camera control unit, coupled to the camera, for receiving and processing the endoscope parameters and endoscope use history data.

In still another advantageous embodiment of the present invention, a method is provided for communicating endoscope parameters and use characteristics from an endoscope, having a memory device and a first transponder/transceiver coupled to the memory device, to a camera control unit, and communicating modified endoscope use characteristics from the camera control unit to the endoscope comprising the steps of: storing a plurality of endoscope parameters and endoscope use characteristics in the memory device; providing a camera with a second transponder/transceiver; coupling the second transponder/transceiver to the camera control unit; retrieving the endoscope parameters and endoscope use characteristics from the memory device; transmitting a first wireless signal containing the endoscope parameters and endoscope use characteristics from the first transponder/transceiver; receiving the first wireless signal at the second transponder/transceiver; transferring the endoscope parameters and endoscope use characteristics contained in the first wireless signal from the camera head to the camera control unit; transferring modified endoscope use characteristics from the camera control unit to the camera; transmitting a second wireless signal containing the modified endoscope use characteristics from the second transponder/transceiver to the first transponder/transceiver; receiving the second wireless signal containing the modified endoscope use characteristics; and storing the modified endoscope use characteristics in the memory device memory locations.

In a further advantageous embodiment of the present invention, an endoscope video system is provided for communicating between an endoscope and a detachable camera comprising: a first transponder/transceiver attached to the endoscope for transmitting and receiving first data; a second transponder/transceiver attached to the detachable camera for transmitting and receiving second data; and a memory device coupled to the first transponder/transceiver having memory locations for storing data.

The invention and its particular features and advantages will become more apparent from the following detailed description considered with reference to the accompanying drawings.

DETAILED DESCRIPTION OF THE INVENTION

Figure 1:
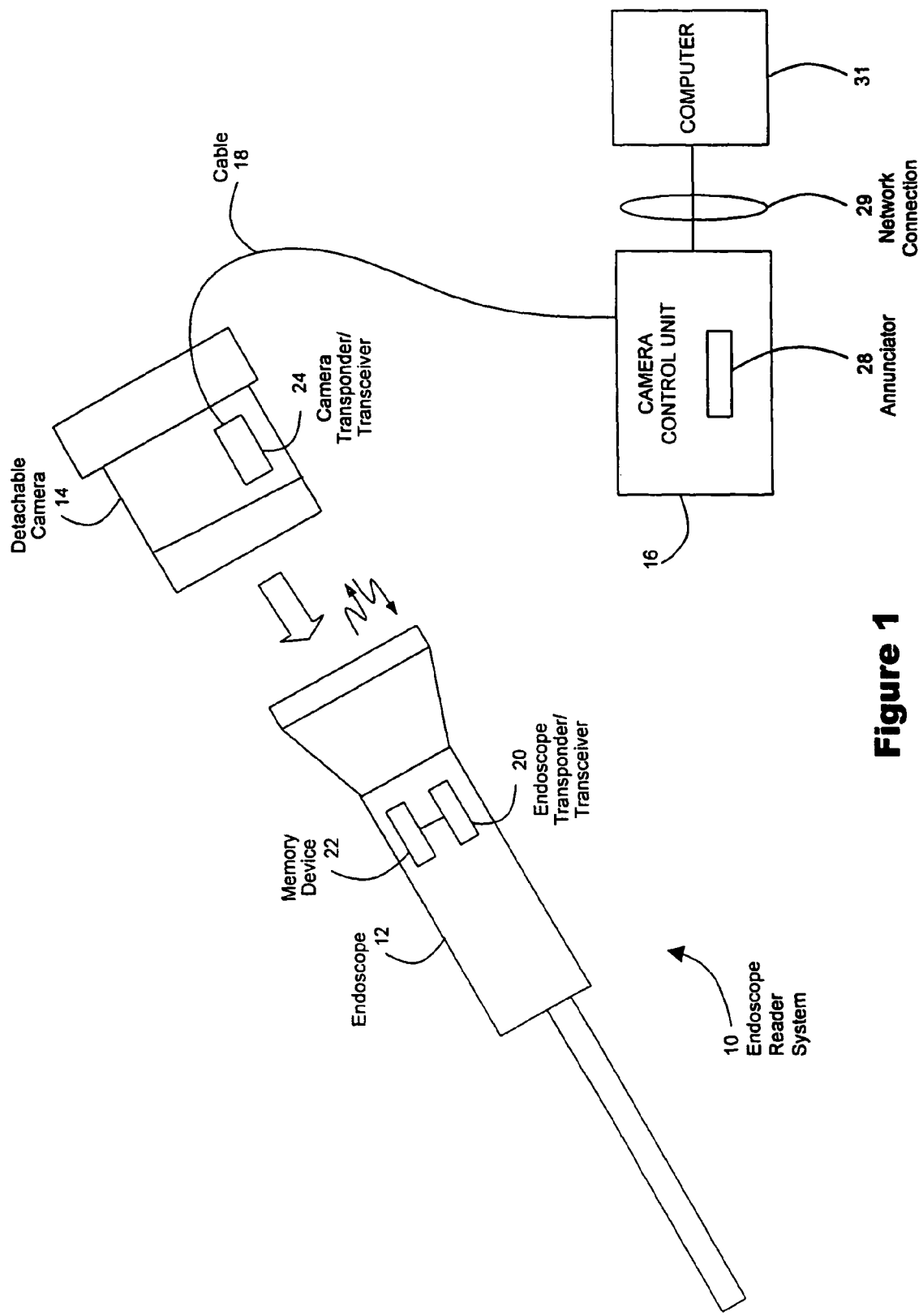
FIG. 1 is an illustration of the assembly of a detachable camera to an endoscope.

Referring now to the drawings, wherein like reference numerals designate corresponding structure throughout the views.

FIG. 1 illustrates an endoscope system 10 for storing and transmitting electronic representations of endoscope characteristics. In accordance with one advantageous embodiment, an endoscope transponder/transceiver 20 is mounted on an endoscope 12 and communicates with a camera head transponder/transceiver 24 mounted on a detachable camera head 14. Endoscope transponder/transceiver 20 and camera head transponder/transceiver 24 may be one of any type of relatively short-range devices well known to those of ordinary skill in the art. Endoscope transponder/transceiver 20 and camera head transponder/transceiver 24 are set so that each is capable of both sending and receiving wireless signals to and from the other.

In one advantageous embodiment, transponder/transceiver 20 and 24 are provided as Radio Frequency (RF) transceivers capable of generating, transmitting and receiving RF signals whether RFID High-Frequency (HF) or Ultra-High Frequency (UHF).

In another advantageous embodiment, transponder/transceiver 20 and 24 may be provided to generate, transmit and receive wireless signals via a standard called IEEE 1902.1, which is also known as the "RuBee" format. Where traditional RFID tags are backscattered transponders, RuBee operates as an active transceiver. RuBee is a bidirectional, on-demand, peer-to-peer, radiating, transceiver protocol operating at wavelengths below 450 KHz. This protocol is advantageous in harsh environments with networks of many thousands of tags and may have an area range of from 10 to about 50 feet.

RuBee offers a real-time, tag-searchable protocol using IPv4 addresses and subnet addresses linked to asset taxonomies that run at speeds of 300 to 9,600 Baud. RuBee Visibility Networks may also be managed by a low-cost Ethernet enabled router. Individual tags and tag data may be viewed as a stand-alone, web server from anywhere in the world. Each RuBee tag, if properly enabled, can be discovered and monitored over the World Wide Web using popular search engines (e.g., Google) or via the Visible Asset's tag Tag Name Server.

Where a network connection 29 is utilized, it is contemplated that the network may be or include any one or more of, for instance, the Internet, an intranet, a LAN (Local Area Network), a WAN (Wide Area Network) or a MAN (Metropolitan Area Network), a frame relay connection, an Advanced Intelligent Network (AIN) connection, a synchronous optical network (SONET) connection, a digital T1, T3 or E1 line, Digital Data Service (DDS) connection, DSL (Digital Subscriber Line) connection, an Ethernet connection, an ATM (Asynchronous Transfer Mode) connection, FDDI (Fiber Distributed Data Interface) or CDDI (Copper Distributed Data Interface) connections and so forth. In this manner, the camera control unit 16 may be coupled to, for example, a remote computer 31 via the network connection 29 for remote access to the data and/or information transmitted to and from endoscope 12.

Another advantage of RuBee is that it can work well through liquids and metals and consumes less power. From a price perspective, RuBee and traditional RFID are similar in cost.

Endoscope transponder/transceiver 20 is coupled to a memory device 22. Memory device 22 is capable of storing and providing electronic representations of parameters of endoscope 12 to endoscope transponder/transceiver 20. Memory device 22 may be of any type that is programmable by such means as electrically, magnetically, by light frequencies or any type that is commonly known to those of ordinary skill in the art.

As mentioned above, camera head 14 is detachable from endoscope 12 and may be attached to other endoscopes. Camera head 14 is coupled to a camera control unit ("CCU") 16 by cable 18. However, camera head 14 can be coupled to CCU 16 by, for instance; a cable connection, including analog, digital or optical; or a wireless connection. Cable 18 couples CCU 16 to camera head 14 and therefore with camera head transponder/transceiver 24. An annunciator 28 may be incorporated into CCU 16 for the purpose of communicating endoscope parameters to personnel operating the endoscope system 10.

Annunciator 28 provides a means by which information concerning the endoscope is communicated to personnel operating the equipment. The annunciator may be a lamp, audible signal, alphanumeric display or other such communication device. Preferably, applicable endoscope parameters received by CCU 16 will subsequently be decoded and displayed on a video monitor for viewing by the endoscope system 10 operator. It is contemplated that memory device 22 may be queried through the present invention by an external computer (not shown) and stored data in memory device 22 retrieved for compilation and analysis. Power for the endoscope mounted circuitry, transponder/transceiver 20 and memory device 22 may be supplied by a power signal from camera head transponder/transceiver 24 derived from a signal from camera head 14, or from an external computer.

Components such as endoscope transponder/transceiver 20, camera head transponder/transceiver 24 and memory device 22, are selected and protected such that they will not be damaged during sterilization of either endoscope 12 or camera head 14. The sterilization may comprise any or all methods of high temperature, chemical or irradiation commonly used in the field. Components employed in endoscope transponder/transceiver 20, memory device 22 and camera head transponder/transceiver 24 must not be degraded by temperatures commonly employed in autoclaves, chemicals such as gluteraldehyde or ethylene oxide, gamma radiation, or any other such sterilization techniques known to those of ordinary skill in the art.

It is also contemplated that various sensors mounted in endoscope 22 will record on memory device 22 peak values that the endoscope 22 is exposed to. This will enable manufacturers and maintenance personnel to determine reasons for endoscope failures and periods for necessary maintenance based upon usage.

It is further contemplated that the endoscope system 10 user will be able to manually "mark" a particular endoscope with a "maintenance required" signal if it is determined by the user that maintenance of the particular endoscope is required. The "marking" can be facilitated by a button or switch locally mounted to the system. Alternatively, the "marking" may take place automatically by the system based upon predetermined criteria. The criteria may include, but is not limited to, elapsed time of use, a certain number of actuations upon receipt of exceeded peak value measurements, or an extended period of time since last maintenance. This "mark" will be transmitted by the endoscope to the CCU and may conspicuously appear on the video screen for future users to see.

The memory device 22 is write-protected such that only factory personnel and/or equipment can remove the "maintenance required" indication. This may be accomplished, for instance, by requiring specific equipment to erase the "maintenance required" indication or by means of a predetermined code that first must be input to enable the removal of the "maintenance required" indication. This will ensure that users of the endoscope system 10 utilize only factory-authorized personnel to repair and maintain the endoscope system 10, which will help to ensure a higher standard of service.

Figure 2:
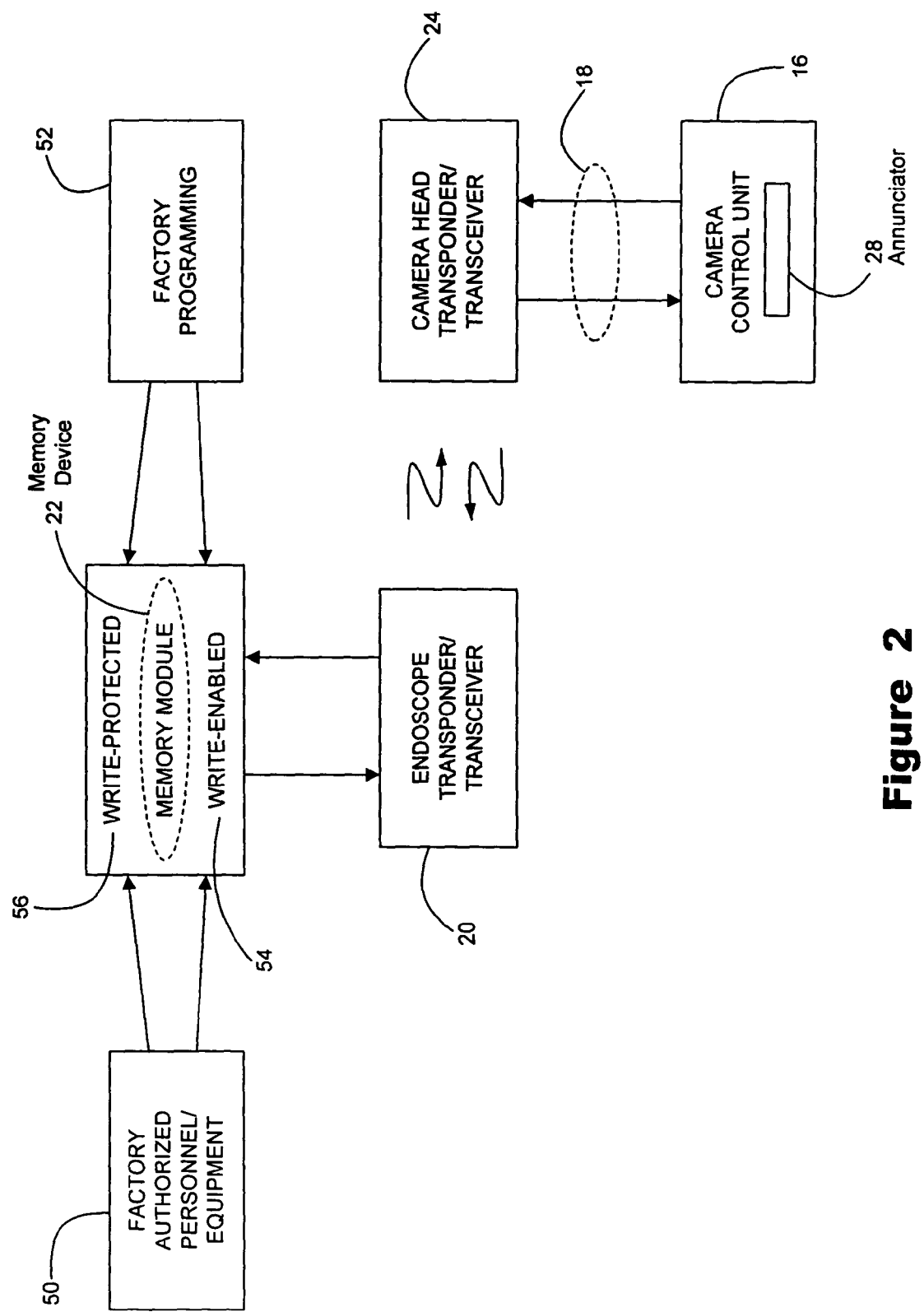
FIG. 2 illustrates the programming of the endoscope memory device and communication with the detachable camera head.

Referring to FIG. 2, memory device 22 stores and supplies electronic representations of endoscope parameters and endoscope use history data. These parameters and data provide a variety of information concerning the endoscope. Information stored in the endoscope would provide all required data for optimal use of the endoscope. In this way, the CCU 16, or other connected medical equipment, would not have to locally or remotely store and access data related to a vast array of different endoscopes. Moreover, as endoscopes are modified and/or improved, corresponding parameters and data are immediately accessible at the time of endoscope use.

The endoscope parameters are broadly classified as fixed or unchanging information. Examples of fixed or unchanging endoscope parameters may include endoscope model and serial number, image relay optics type (e.g., rod lens, fused quartz, fiber optic), endoscope size, optical properties such a field of view, signal processing data for use by the CCU 16 for video signal optimization, maintenance requirements and interval, settings information for other medical equipment (such as high intensity light sources or insufflators) which are connected and/or controlled by the CCU 16 via a communication bus or any variety of characteristics that may be useful in endoscope, video camera system and other medical equipment usage.

The endoscope use history data is broadly classified as variable or updateable. Examples of variable or updateable endoscope use history data may include, for instance, number of endoscope usages, time of each endoscope use, total time of endoscope operation, number of actuations and medical equipment (used with the endoscope) identification and settings information.

Memory device 22 locations are broadly classified as write-enabled 54 and write-protected 56. Memory device 22 can be capable of disallowing changes to memory locations until specified conditions are met. These conditions may be electrical such as requiring injection of a known signal or series of signals, or programmatic such as a password or any similar such method to prevent unauthorized alteration of the memory device locations. Write-protected locations store parameters that may be altered only during factory programming 52, or by factory authorized personnel/equipment 50. These endoscope parameters are generally, but not necessarily, fixed or unchanging as enumerated above. Write-enabled locations may be altered during factory programming 52, by factory authorized personnel/equipment 50, or with electronic representations of data received from the endoscope transponder/transceiver 20.

Endoscope transponder/transceiver 20 communicates with camera head transponder/transceiver 24 once the camera head transponder/transceiver 24 comes into close proximity. As previously described, power for the endoscope transponder/transceiver 20 is supplied from the camera head transponder/transceiver 24. Transceivers supplied with power in this manner typically have short ranges as compared to similar devices with their own power sources. It is anticipated that the effective range of transmission of the endoscope transponder/transceiver 20 and the camera head transponder/transceiver 24 may advantageously be very short. This is beneficial since an extensive transmission area could disadvantageously result in an endoscope communicating with an unrelated camera head or cause other communication problems with other equipment in the operating room. For example, if the RuBee signal format is utilized, it is contemplated that the signal range will extend from approximately 10 feet to approximately 50 feet.

Camera head transponder/transceiver 24 also exchanges signals with CCU 16 via cable 18. CCU 16 may present the received signals on annunciator 28. For example, data indicating that maintenance of the endoscope is required may be provided by endoscope transponder/transceiver 20 to camera head transponder/transceiver 24 which is forwarded to CCU 16 that, in turn, presents an alert to annunciator 28 that endoscope maintenance is required.

Figure 3:
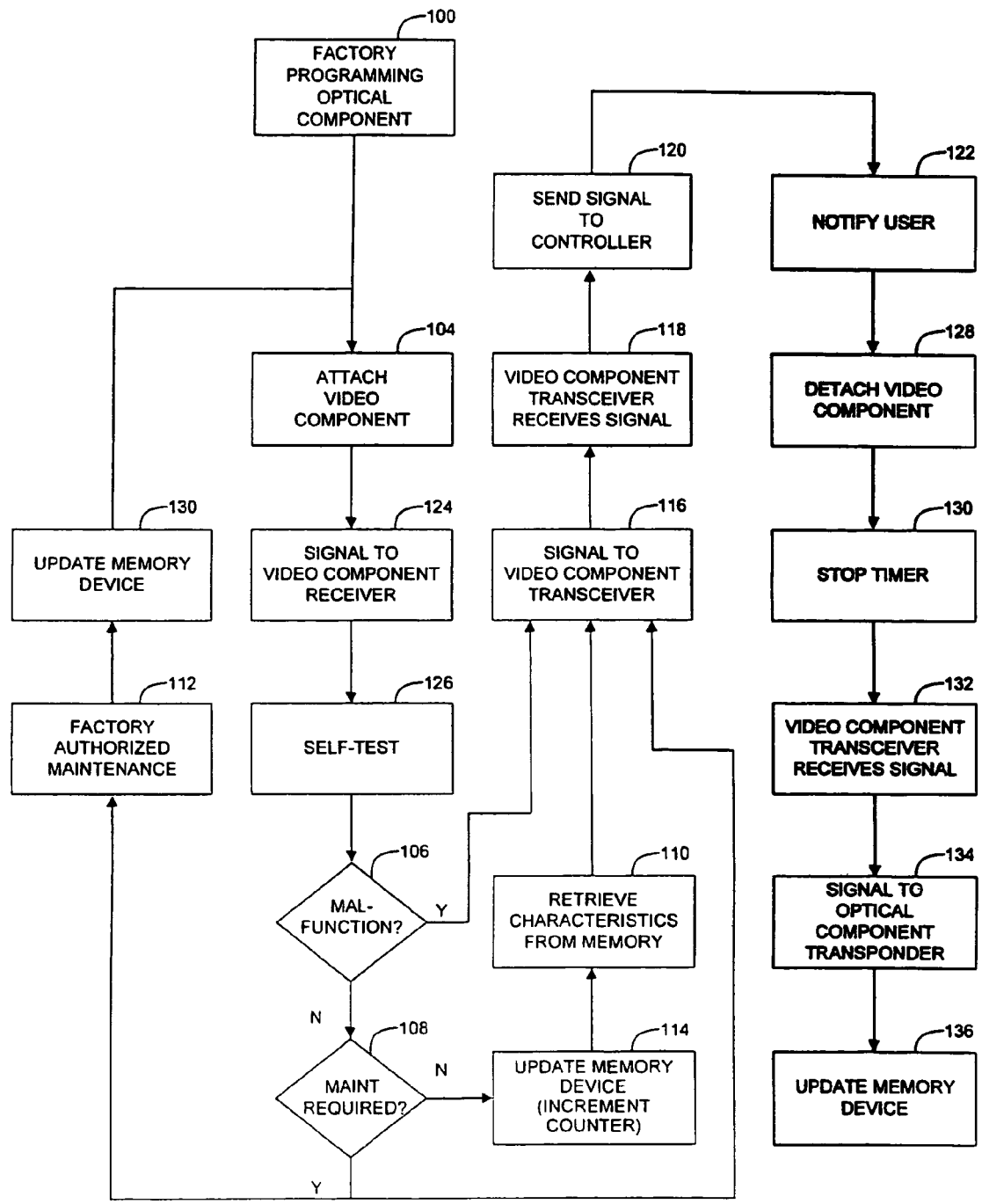
FIG. 3 illustrates a block diagram for implementing the method of the present invention.

FIG. 3 illustrates another application of the present invention. At 100, during manufacture of the endoscope, a memory device mounted in or on the endoscope is programmed with electronic representations of parameters and data specific to that particular endoscope 105. These parameters may include the optical properties, serial number, model number, maintenance schedule, required camera settings, required equipment settings, malfunction codes and other such characteristics and parameters. The memory device will have sufficient additional memory locations to store other data as described below.

Once a camera head is energized, that is, "powered on," a short-range wireless signal is radiated from the camera head transponder/transceiver. Upon the energized camera head being attached to a particular endoscope 110, the wireless signal radiating from the camera head transponder/transceiver powers the endoscope transponder/transceiver. Consequently, the endoscope transponder/transceiver energizes the endoscope memory device, which provides the electronic representation of the endoscope parameters to the endoscope transponder/transceiver with the camera head transponder/transceiver receiving the wireless signal containing the electronic representation of the endoscope parameters from the endoscope transponder/transceiver 115. The CCU, connected to the camera head, decodes the electronic representations of the endoscope parameters and thus "identifies" the endoscope in use. Specific information can then be communicated to the system user 120, such as, but not limited to, endoscope type/model or serial number. The communication may be a visual indicator, an alphanumeric display or printout, an audio signal or any such communication technique. Preferably, the information is displayed on the system video monitor. If the endoscope attached to the camera head does not have a transponder/transceiver and programmed memory device, the video system configuration will remain unchanged.

Once the endoscope is identified and the endoscope parameters are loaded to the CCU, the CCU analysis and increments a "times used" counter (data) 125 for tracking and updating the count of how many times the endoscope was used with an endoscope reader compatible video system. The updated use count data is then written to the endoscope memory device as modified endoscope use history data by means of the camera head transponder/transceiver and the endoscope transponder/transceiver 130.

The amount of time that an endoscope is in use determines the necessity for maintenance, as well as providing statistical data for factory use in design and marketing. Concurrent with the incrementing of the "times used" counter, the CCU also starts an elapsed time ("time in use") clock 135. The elapsed time continues to accumulate as long as the camera head is attached to the endoscope. Periodically, throughout the current use of the endoscope, the CCU, by means of the camera head transponder/transceiver and endoscope transponder/transceiver, updates the endoscope memory device 130 with modified endoscope use history data containing new accumulated "time in use" data 135. In this way, the total "time in use" corresponding to a particular use of the endoscope is stored in the endoscope memory device.

Based upon endoscope parameters extracted from the endoscope memory device, the maintenance status of the endoscope 140 is determined by the CCU. The maintenance requirements criteria, endoscope use history data and any other datum items required for the CCU to determine the current status of the endoscope was previously received by the CCU from the endoscope memory device at 115. If the CCU determines that endoscope maintenance is required 145, the maintenance related information is communicated to the user 150. The communication may be a visual indicator, an alphanumeric display or printout, an audio signal or any such communication technique. Preferably, the information is displayed on the system video monitor.

Depending upon the type of endoscope maintenance required, the user may, be provided the option to continue using the endoscope 160. If the user opts to continue, information pertaining to the continuation is then written to the endoscope memory device by means of the camera head transponder/transceiver and the endoscope transponder/transceiver 130. If the user opts not to continue endoscope use 165 or the continuation option 155 is not provided to the user, it is anticipated that the endoscope will be sent for factory authorized maintenance 170. When the maintenance is completed, the memory device is updated 105 so that the routine maintenance requirements are reset and the video system no longer reports that maintenance is required. The endoscope is again ready for camera head attachment 110 and use.

If endoscope maintenance is not required 175 at 140 or the user opts to continue using the endoscope 160 at 155, the CCU adjusts video processing settings 180 in order to optimize the video system according to endoscope parameters previously retrieved at 115. Additionally, other medical equipment, such as light sources or insufflators settings, may be optimized 180 according to endoscope parameters, as previously described.

Further information gathered, analyzed and compiled may be included in the endoscope use history data by the CCU for storage in the endoscope memory device 130. Endoscope use history data may include data on what camera head, CCU and other medical equipment was used with the endoscope (to include equipment serial numbers, model numbers, software revision numbers, etc.). Any information, which may be useful in determining how well an endoscope functioned, or under what conditions the endoscope functioned, could be included in the endoscope use history data. The endoscope use history data could later be retrieved for demographic or performance analysis purposes. An example is as follows. If a particular endoscope causes numerous CCUs to set exposure levels above a nominal value, this may indicate that the endoscope is not properly relaying images to the camera head. This CCU exposure level data would be included in the endoscope use history data and stored in the endoscope memory device. A review of the stored data would reveal this operational "trend," the endoscope could be inspected and, if necessary, repaired before a catastrophic failure occurs.

As previously described, periodically, the CCU updates the endoscope memory device 130 with modified endoscope use history data containing new accumulated "time in use" data 135. When the camera head is detached from the endoscope 190, the last accumulated "time in use" data will already have been stored in the endoscope memory device. The interval at which the "time in use" data is updated in the endoscope memory device would be frequent enough (i.e., every few minutes or every minute) to ensure the accuracy of the data prior to the camera head being detached from the endoscope.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An endoscope video system for communicating between an endoscope and a detachable camera comprising:
    an endoscope having a first transponder/transceiver positioned thereon, the first transponder/transceiver transmitting and receiving wireless signals;
    a memory device positioned on said endoscope and coupled to the first transponder/transceiver;

a camera having a second transponder/transceiver positioned thereon, the second transponder/transceiver wirelessly coupling to the first transponder/transceiver when brought in proximity thereto to transmit and receive wireless signals;

said wireless signals comprising endoscope parameter data and endoscope use history data and modified endoscope use history data;

a camera control unit, coupled to the camera, said camera control unit receiving and processing the endoscope parameter data and endoscope use history data, said camera control unit generating and transmitting the modified endoscope use history data.

2. The endoscope video system of claim 1 wherein the wireless transmission format between the first transponder/transceiver and the second transponder /transceiver is selected from the group consisting of: RuBee, Radio Frequency Identification (RFID) and combinations thereof.

3. The endoscope video system of claim 2 wherein when the RuBee format is utilized, said camera control unit further comprises a connection to a network for transmission of the endoscope parameter data, the endoscope use history data and the modified endoscope use history data to a remote computer.

4. The endoscope video system of claim 3 wherein the network is selected from the group consisting of: the Internet, an intranet, a LAN, a WAN, a MAN and combinations thereof.

5. The endoscope video system of claim 1 wherein the endoscope parameters comprise endoscope specification data, video system configuration data and maintenance requirements data.

6. The endoscope video system of claim 1 wherein the camera control unit automatically adjusts its operational settings in accordance with the received endoscope parameters.

7. The endoscope video system of claim 1 wherein the camera control unit, upon receiving the endoscope parameters and endoscope use history data, modifies at least one endoscope use history data value indicating that a detachable camera has been attached to the endoscope, and providing modified endoscope use history data to the second transponder/transceiver for transmission to the first transponder/transceiver and storage in the memory device.

8. An endoscope video system providing for the transfer of data from an endoscope comprising:
    an endoscope having a transponder/transceiver positioned thereon, the transponder/transceiver transmitting a wireless signal including endoscope parameter data and endoscope use history data, and receiving a wireless signal containing modified endoscope use history data; and
    a memory device positioned on said endoscope and coupled to the transponder/transceiver, said memory device storing the modified endoscope use history data.

9. The endoscope video system of claim 8 wherein the wireless transmission format of the transponder/transceiver is selected from the group consisting of: RuBee, Radio Frequency Identification (RFID) and combinations thereof.

10. The endoscope video system of claim 8 wherein the system further comprises a camera control unit coupled to a network and transmitting the endoscope parameter data, the endoscope use history data and the modified endoscope use history data to a computer.

11. The endoscope video system of claim 10 wherein the network is selected from the group consisting of: the Internet, an intranet, a LAN, a WAN, a MAN and combinations thereof.

12. The endoscope video system of claim 8 wherein the endoscope parameters include endoscope specification data, video system configuration data and maintenance requirements data.

13. The endoscope video system of claim 8 wherein operational settings of the camera control unit are automatically adjusted based on the received endoscope parameters.

14. A method of communicating between an endoscope and a detachable camera comprising the steps of:
    positioning a first transponder/transceiver on an endoscope;
    positioning a memory device on the endoscope;
    coupling the memory device to the first transponder/transceiver;
    positioning a second transponder/transceiver on a camera;
    coupling the camera to a camera control unit;
    detachably coupling the endoscope to the camera;
    wirelessly coupling the first transponder/transceiver to the second transponder/transceiver when positioned in proximity to each other;
    wirelessly transmitting endoscope parameter data and endoscope use history data from the first transponder/transceiver to the second transponder/transceiver;
    transmitting the endoscope parameter data and endoscope use history data from the camera to the camera control unit;
    transmitting modified endoscope use history data from the camera control unit to the camera;
    wirelessly transmitting the modified endoscope use history data from the second transponder/transceiver to the first transponder/transceiver; and
    storing the modified endoscope use history data in the memory device.

15. The method of claim 14 wherein the wireless transmission format between the first transponder/transceiver and the second transponder/transceiver is selected from the group consisting of: RuBee, Radio Frequency Identification (RFID) and combinations thereof.

16. The method of claim 15 wherein when the RuBee format is utilized, the method further comprises the step of coupling the camera control unit to a network and transmitting the endoscope parameter data, the endoscope use history data and the modified endoscope use history data to a remote computer.

17. The method of claim 16 wherein the network is selected from the group consisting of: the Internet, an intranet, a LAN, a WAN, a MAN and combinations thereof.

18. The method of claim 17 wherein the endoscope parameters include endoscope specification data, video system configuration data and maintenance requirements data.

19. The method of claim 14 further comprising the steps of automatically adjusting the operational settings of the camera control unit based on the received endoscope parameters.

20. An endoscope video system for communicating between an endoscope and a detachable camera comprising:
    an endoscope having a first transponder/transceiver positioned thereon, the first transponder/transceiver transmitting and receiving wireless signals;
    a memory device positioned on said endoscope and coupled to the first transponder/transceiver;
    a camera having a second transponder/transceiver positioned thereon, the second transponder/transceiver wirelessly coupling to the first transponder/transceiver when brought in proximity thereto to transmit and receive wireless signals;
    said wireless signals comprising image data;

a camera control unit, coupled to the camera, said camera control unit receiving and processing the image data.

21. The endoscope video system of claim 20 wherein said wireless signals further comprise endoscope parameter data and endoscope use history data and modified endoscope use history data.

22. The endoscope video system of claim 21 wherein the endoscope parameters comprise endoscope specification data, video system configuration data and maintenance requirements data.

23. The endoscope video system of claim 21 wherein the camera control unit, upon receiving the endoscope parameters and endoscope use history data, modifies at least one endoscope use history data value indicating that a detachable camera has been attached to the endoscope, and providing modified endoscope use history data to the second transponder/transceiver for transmission to the first transponder/transceiver and storage in the memory device.

24. The endoscope video system of claim 23 wherein when the RuBee format is utilized, said camera control unit further comprises a connection to a network for transmission of the endoscope parameter data, the endoscope use history data and the modified endoscope use history data to a remote computer.

25. The endoscope video system of claim 21 wherein the wireless transmission format between the first transponder/transceiver and the second transponder/transceiver is selected from the group consisting of: RuBee, Radio Frequency Identification (RFID) and combinations thereof.

26. The endoscope video system of claim 25 wherein the network is selected from the group consisting of: the Internet, an intranet, a LAN, a WAN, a MAN and combinations thereof.

27. The endoscope video system of claim 16 wherein the camera control unit automatically adjusts its operational settings in accordance with the received endoscope parameters.

* * * * *